(12) United States Patent
Lappin

(10) Patent No.: US 11,957,594 B2
(45) Date of Patent: Apr. 16, 2024

(54) REVERSE SHOULDER ORTHOPAEDIC IMPLANT HAVING AN ELLIPTICAL GLENOSPHERE COMPONENT

(71) Applicant: DEPUY SYNTHES PRODUCTS, INC., Raynham, MA (US)

(72) Inventor: Kyle E. Lappin, Fort Wayne, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 17/701,075

(22) Filed: Mar. 22, 2022

(65) Prior Publication Data

US 2022/0211510 A1 Jul. 7, 2022

Related U.S. Application Data

(60) Continuation of application No. 16/390,475, filed on Apr. 22, 2019, now Pat. No. 11,278,418, which is a continuation of application No. 14/560,654, filed on Dec. 4, 2014, now Pat. No. 10,265,184, which is a division of application No. 13/431,416, filed on Mar. 27, 2012, now abandoned.

(51) Int. Cl.
*A61F 2/40* (2006.01)
*A61F 2/46* (2006.01)
*A61F 2/30* (2006.01)

(52) U.S. Cl.
CPC .............. *A61F 2/40* (2013.01); *A61F 2/4014* (2013.01); *A61F 2/4081* (2013.01); *A61F 2/4612* (2013.01); *A61F 2002/30125* (2013.01); *A61F 2002/30332* (2013.01); *A61F 2002/30494* (2013.01); *A61F 2002/30616* (2013.01); *A61F 2002/30772* (2013.01); *A61F 2002/30878* (2013.01); *A61F 2002/4022* (2013.01); *A61F 2002/4085* (2013.01); *A61F 2002/4681* (2013.01)

(58) Field of Classification Search
CPC ........ A61F 2/40; A61F 2/4014; A61F 2/4081; A61F 2/4612; A61F 2002/30125; A61F 2002/30878; A61F 2002/4085
See application file for complete search history.

(56) References Cited

U.S. PATENT DOCUMENTS

| 4,261,062 | A  | 4/1981  | Amstutz et al. |
| 6,790,234 | B1 | 9/2004  | Frankle |
| 6,875,234 | B2 | 4/2005  | Lipman et al. |
| 6,953,478 | B2 | 10/2005 | Bouttens et al. |

(Continued)

FOREIGN PATENT DOCUMENTS

| DE | 102008053566 A1 | 6/2009 |
| EP | 1064890 A1 | 1/2001 |

(Continued)

OTHER PUBLICATIONS

Indian Examination Report for Indian Application No. 7760/DELNP/2014, dated Jun. 11, 2020, 6 pages.

(Continued)

*Primary Examiner* — Bruce E Snow
(74) *Attorney, Agent, or Firm* — Barnes & Thornburg LLP

(57) ABSTRACT

A reverse shoulder orthopaedic implant includes a glenosphere component having a lateral bearing surface configured to articulate with a humeral cup of a humeral prosthesis. A metaglene component includes a platform configured to receive glenosphere component.

20 Claims, 9 Drawing Sheets

(56) References Cited

U.S. PATENT DOCUMENTS

| | | |
|---|---|---|
| 7,169,184 B2 | 1/2007 | Dalla Pria |
| 7,175,663 B1 | 2/2007 | Stone |
| 7,241,314 B1 | 7/2007 | Winslow |
| 7,462,197 B2 | 12/2008 | Tornier et al. |
| 8,062,376 B2 | 11/2011 | Shultz et al. |
| 8,303,665 B2 | 11/2012 | Tornier et al. |
| 9,078,758 B2 | 7/2015 | Leibel |
| 9,629,724 B2 | 4/2017 | Lappin |
| 10,265,184 B2 | 4/2019 | Lappin |
| 2004/0220674 A1 | 11/2004 | Pria |
| 2005/0256584 A1 | 11/2005 | Farrar |
| 2005/0261775 A1 | 11/2005 | Baum et al. |
| 2006/0241775 A1 | 10/2006 | Buss |
| 2007/0225818 A1 | 9/2007 | Reubelt et al. |
| 2009/0281630 A1 | 11/2009 | Delince et al. |
| 2010/0023068 A1 | 1/2010 | Bouttens et al. |
| 2010/0087927 A1 | 4/2010 | Roche et al. |
| 2012/0029647 A1 | 2/2012 | Winslow et al. |
| 2012/0209392 A1 | 8/2012 | Angibaud et al. |
| 2012/0253467 A1 | 10/2012 | Frankle |
| 2012/0277880 A1 | 11/2012 | Winslow et al. |
| 2013/0150973 A1 | 6/2013 | Splieth et al. |
| 2019/0240035 A1 | 8/2019 | Lappin |

FOREIGN PATENT DOCUMENTS

| | | |
|---|---|---|
| EP | 1656910 A1 | 5/2006 |
| EP | 1996123 A2 | 12/2008 |
| EP | 1711132 B1 | 8/2009 |
| FR | 2541890 A1 | 9/1984 |
| FR | 2579454 A1 | 10/1986 |
| FR | 2652498 A1 | 4/1991 |
| FR | 2674122 A1 | 9/1992 |
| FR | 2737107 A1 | 1/1997 |
| FR | 2832922 A1 | 6/2003 |
| FR | 2871369 A1 | 12/2005 |
| FR | 2937245 A1 | 4/2010 |
| GB | 2325626 A | 12/1998 |
| JP | 07196433 A | 8/1995 |
| WO | 02067821 A2 | 9/2002 |
| WO | 2007109291 A2 | 9/2007 |
| WO | 2007109800 A2 | 9/2007 |

OTHER PUBLICATIONS

Supplementary European Search Report for EP 07 75 3578 dated Nov. 20, 2009, 2 pages.

Patent Cooperation Treaty (PCT) International Search Report, International Application No. PCT/2013/033128, dated May 14, 2013, 5 pages.

REVERSE SHOULDER ORTHOPAEDIC IMPLANT HAVING AN ELLIPTICAL GLENOSPHERE COMPONENT

This application is a continuation application of U.S. patent application Ser. No. 16/390,475, now U.S. Pat. No. 11,278,418, which was filed on Apr. 22, 2019, which is a continuation application of U.S. patent application Ser. No. 14/560,654, now U.S. Pat. No. 10,265,184, which was filed on Dec. 4, 2014 and which is a divisional application of U.S. patent application Ser. No. 13/431,416, which was filed on Mar. 27, 2012, each of which is expressly incorporated herein by reference.

CROSS-REFERENCE TO RELATED U.S. PATENT APPLICATION

Cross reference is made to U.S. patent application Ser. No. 13/431,406, now U.S. Pat. No. 8,945,229, entitled "REVERSE SHOULDER ORTHOPAEDIC IMPLANT HAVING A METAGLENE COMPONENT WITH A SCREW LOCKING CAP" by Kyle Lappin, which is assigned to the same assignee as the present invention.

TECHNICAL FIELD

The present disclosure relates generally to orthopaedic implants, and more particularly to reverse shoulder orthopaedic implants.

BACKGROUND

During the lifetime of a patient, it may be necessary to perform a total shoulder replacement procedure on the patient as a result of, for example, disease or trauma. In a total shoulder replacement procedure, a humeral prosthesis is used to replace the natural head of the patient's humerus. The humeral prosthesis typically includes an elongated stem component that is implanted into the intramedullary canal of the patient's humerus and a hemispherically-shaped prosthetic head component that is secured to the stem component. In such a total shoulder replacement procedure, the natural glenoid surface of the scapula is resurfaced or otherwise replaced with a glenoid component that provides a bearing surface upon which the prosthetic head component of the humeral prosthesis articulates.

However, in some cases the patient's natural shoulder, including its soft tissue, has degenerated to a severe degree of joint instability and pain. In many such cases, it may be necessary to change the mechanics of the shoulder. Reverse shoulder implants are used to do so. As its name suggests, a reverse shoulder implant reverses the anatomy, or structure, of the healthy shoulder. In particular, a reverse shoulder implant is designed such that the prosthetic head (i.e., the "ball" in the ball-and-socket joint) known as a glenosphere component is secured to the patient's scapula, with the corresponding concave bearing (i.e., the "socket" in the ball-and-socket joint) known as a humeral cup being secured to the patient's humerus. Such a reverse configuration allows the patient's deltoid muscle, which is one of the larger and stronger shoulder muscles, to raise the arm.

SUMMARY

According to one aspect, a reverse shoulder orthopaedic implant includes a glenosphere component having a curved lateral bearing surface configured to articulate with a humeral cup of a humeral prosthesis, and a medial surface having a tapered bore formed therein. The glenosphere component has an anterior/posterior width defined by the distance between an anterior-most point of the lateral bearing surface and a posterior-most point of the lateral bearing surface, and a superior/inferior width defined by the distance between a superior-most point of the lateral bearing surface and an inferior-most point of the lateral bearing surface. The anterior/posterior width of the glenosphere component is greater than its superior/inferior width.

The lateral bearing surface of the glenosphere component may be hemi-ellipsoidal in shape. The glenosphere component may be metallic.

An imaginary line segment extends from a superior-most point of the medial surface to an inferior-most point of the medial surface. The center of the tapered bore may be positioned between the midpoint of the imaginary line segment and the superior-most point of the medial surface. Alternatively, the center of the tapered bore may be positioned at the midpoint of the imaginary line segment.

The reverse shoulder orthopaedic implant may also include a metaglene component having an annular-shaped platform with an elongated stem extending outwardly from a medial surface thereof. A tapered outer surface of the annular-shaped platform may be taper locked in the tapered bore of the glenosphere component.

According to another aspect, a reverse shoulder orthopaedic implant includes a glenosphere component having a curved lateral bearing surface configured to articulate with a humeral cup of a humeral prosthesis, and a medial surface having a bore formed therein to receive a metaglene component. The glenosphere component has an anterior/posterior width defined by the distance between an anterior-most point of the glenosphere component and a posterior-most point of the glenosphere component, and a superior/inferior width defined by the distance between a superior-most point of the glenosphere component and an inferior-most point of the glenosphere component. The anterior/posterior width of the glenosphere component is greater than the superior/inferior width of the glenosphere component.

The lateral bearing surface of the glenosphere component may be hemi-ellipsoidal in shape. The glenosphere component may be metallic.

An imaginary line segment extends from a superior-most point of the medial surface to an inferior-most point of the medial surface. The center of the bore may be positioned between the midpoint of the imaginary line segment and the superior-most point of the medial surface. Alternatively, the center of the bore may be positioned at the midpoint of the imaginary line segment.

The reverse shoulder orthopaedic implant may also include a metaglene component having an annular-shaped platform with an elongated stem extending downwardly from a lower surface thereof. The bore formed in the glenosphere component may include a tapered bore, with a tapered outer surface of the annular-shaped platform being taper locked in such a tapered bore.

According to another aspect, a reverse shoulder orthopaedic implant includes a glenosphere component having a lateral bearing surface configured to articulate with a humeral cup of a humeral prosthesis. The lateral bearing surface is hemi-ellipsoidal in shape with its longitudinal axis extending in the anterior/posterior direction. The reverse shoulder orthopaedic implant also includes a metaglene component secured to the glenosphere component.

An anterior/posterior width of the glenosphere component may be defined by the distance between an anterior-most point of the lateral bearing surface and a posterior-most point of the lateral bearing surface, with its superior/inferior width being defined by the distance between a superior-most point of the lateral bearing surface and an inferior-most point of the lateral bearing surface. The anterior/posterior width of the glenosphere component is greater than the superior/inferior width of the glenosphere component.

A tapered bore may be formed in the medial surface of the glenosphere component, with a tapered outer surface of the metaglene component being taper locked therein.

An imaginary line segment extends from a superior-most point of the medial surface to an inferior-most point of the medial surface. The center of the tapered bore may be positioned between the midpoint of the imaginary line segment and the superior-most point of the medial surface. Alternatively, the center of the tapered bore may be positioned at the midpoint of the imaginary line segment.

Both the glenosphere component and the metaglene component may be metallic.

The platform of the metaglene component may include a number of screw holes extending therethrough.

According to another aspect, a reverse shoulder orthopaedic implant includes a metaglene component having a platform with a number of screw holes extending therethrough, and an elongated stem extending downwardly from a medial surface thereof. The elongated stem is configured to be implanted into the scapula of a patient. The elongated stem has a bore formed therein. The reverse shoulder orthopaedic implant also includes a screw cap having a shaft positioned in the bore of the metaglene component, and a locking flange extending outwardly from the shaft so as to at least partially cover each of the number of screw holes of the metaglene component.

Each of the number of screw holes defines a circumference. An outer edge of the locking flange of the screw cap overlaps at least a portion of the circumference of each of the number of screw holes of the metaglene component.

The bore formed in the elongated stem of the metaglene component may be embodied as a threaded bore and the shaft of the screw cap may be embodied as a threaded shaft that is threaded into the threaded bore of the metaglene component.

The locking flange may be annular shaped, with the shaft extending outwardly from a lower surface of the locking flange. A drive socket may be formed in the upper surface of the locking flange.

The reverse shoulder orthopaedic implant may also include a glenosphere component having a bore formed therein, with the screw cap being captured in the bore of the glenosphere component.

The reverse shoulder orthopaedic implant may also include a retaining ring secured within the bore of the glenosphere component so as to retain the screw cap therein.

The reverse shoulder orthopaedic implant may further include a number of compression screws positioned in the number of screw holes of the metaglene component. Each of such compression screws has a screw head having a round outer edge, with an outer edge of the locking flange of the screw cap overlapping at least a portion of the round outer edge of each of the number of screw holes of the metaglene component.

According to another aspect, a reverse shoulder orthopaedic implant includes a metaglene component having a platform with a number of screw holes extending therethrough, and an elongated stem extending downwardly from a medial surface thereof. The elongated stem has a bore formed therein. The reverse shoulder orthopaedic implant also includes a glenosphere component having a bore formed therein and a screw cap captured in the bore of the glenosphere component. The screw cap is rotatable relative to the glenosphere component. The screw cap has a shaft positioned in the bore of the metaglene component, and a locking flange extending outwardly from the shaft so as to at least partially cover each of the number of screw holes of the metaglene component.

The locking flange of the screw cap may include an annular-shaped beveled surface.

The screw cap may also include a cylindrically-shaped surface extending upwardly from the annular-shaped beveled surface, and a retaining flange extending outwardly from the cylindrically-shaped surface. A retaining ring may be positioned around the cylindrically-shaped surface of the screw cap and secured to the sidewalls of the glenosphere defining the bore. The diameter of the retaining flange of the screw cap is larger than the inner diameter of the retaining ring and smaller than the outer diameter of the retaining ring.

A drive socket is formed in an upper surface of the retaining flange of the screw cap.

The retaining ring may be press fit within the bore of the glenosphere component so as to retain the screw cap therein.

Each of the number of screw holes defines a circumference. An outer edge of the locking flange of the screw cap overlaps at least a portion of the circumference of each of the number of screw holes of the metaglene component.

The bore formed in the elongated stem of the metaglene component may be embodied as a threaded bore and the shaft of the screw cap may be embodied as a threaded shaft that is threaded into the threaded bore of the metaglene component.

The reverse shoulder orthopaedic implant may also include a number of compression screws positioned in the number of screw holes of the metaglene component. The locking flange of the screw cap may include an annular-shaped beveled surface, with each of the number of compression screws has a screw head having a round outer edge. The beveled surface of the locking flange of the screw cap contacts the round outer edge of each of the number of screw holes of the metaglene component.

According to another aspect, a reverse shoulder orthopaedic implant includes a metaglene component configured to be implanted into the scapula of a patient. The metaglene component has a platform with a number of screw holes extending therethrough. A number of compression screws are positioned in the number of screw holes of the metaglene component. Each of the number of compression screws has a screw head with a round outer edge. A screw cap is secured to the metaglene component. The screw cap has a locking flange that includes an outer edge that overlaps at least a portion of the round outer edge of each of the number of screw holes of the metaglene component.

Each of the number of screw holes defines a circumference, with the outer edge of the locking flange of the screw cap overlapping at least a portion of the circumference of each of the number of screw holes of the metaglene component.

The platform of the metaglene component may include an elongated stem with a threaded bore formed therein, with the screw cap having a threaded shaft extending downwardly for a lower surface of the locking flange. The threaded shaft of the screw cap may be threaded into the threaded bore of the metaglene component.

A drive socket may be formed in an upper surface of the screw cap.

BRIEF DESCRIPTION OF THE DRAWINGS

The detailed description particularly refers to the following figures, in which.

DETAILED DESCRIPTION OF THE DRAWINGS

Figure 1:
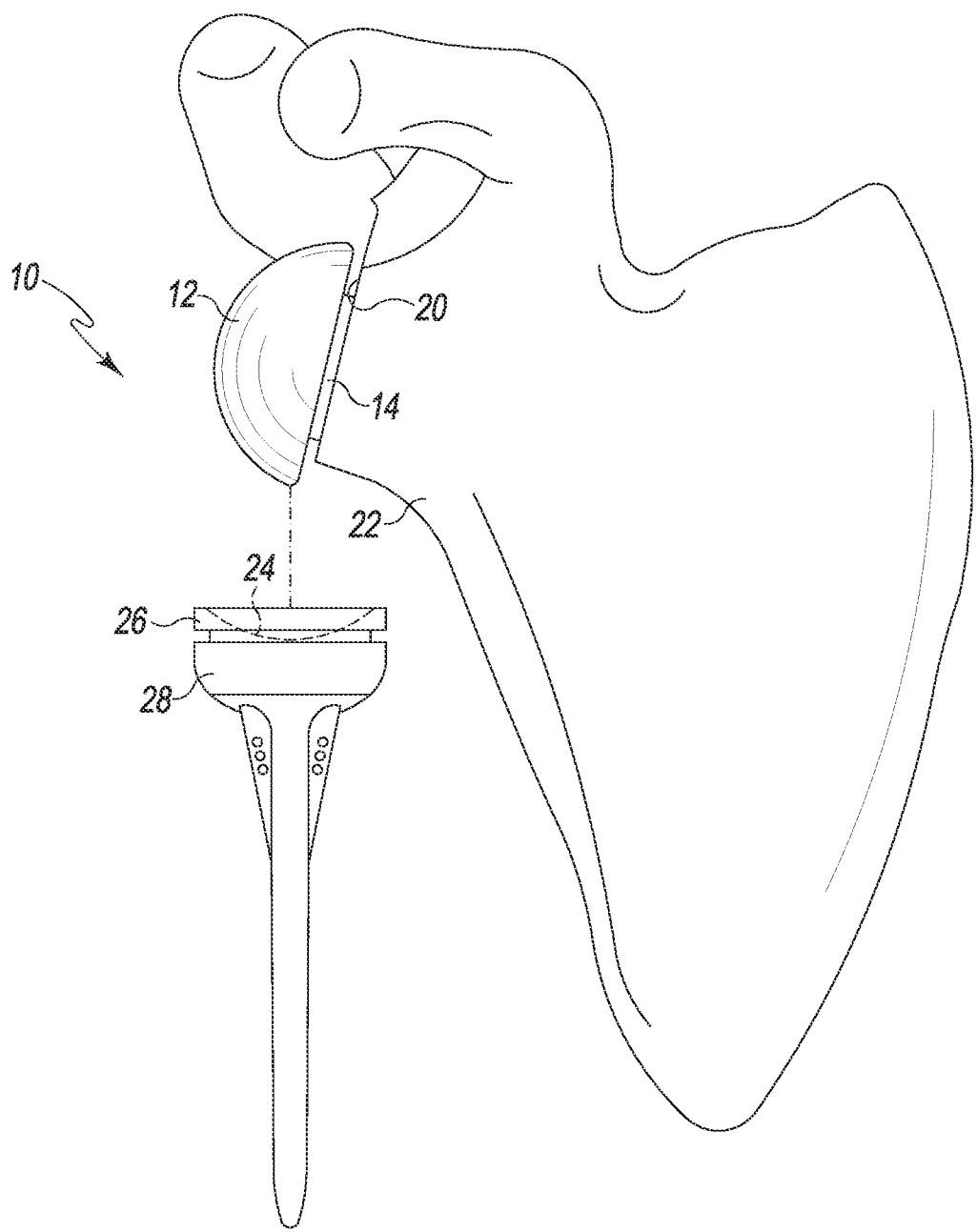
FIG. 1 is an anterior elevational view showing a reverse shoulder orthopaedic implant that has been implanted into the shoulder of a patient.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIGS. 1-6, there is shown a reverse shoulder orthopaedic implant 10 for replacing the natural shoulder joint of a patient. The reverse shoulder orthopaedic implant 10 includes an elliptical glenosphere component 12 that is secured to the glenoid surface 20 of the patient's scapula 22 by a metaglene component 14 implanted in the bone tissue of the scapula 22. The elliptical glenosphere component 12 articulates on the bearing surface 24 of a humeral cup 26 of a humeral prosthesis. As can be seen in FIG. 1, the humeral cup 26 is secured to a humeral stem component 28 that is implanted in the intramedullary canal of a patient's humerus (not shown).

Figure 2:
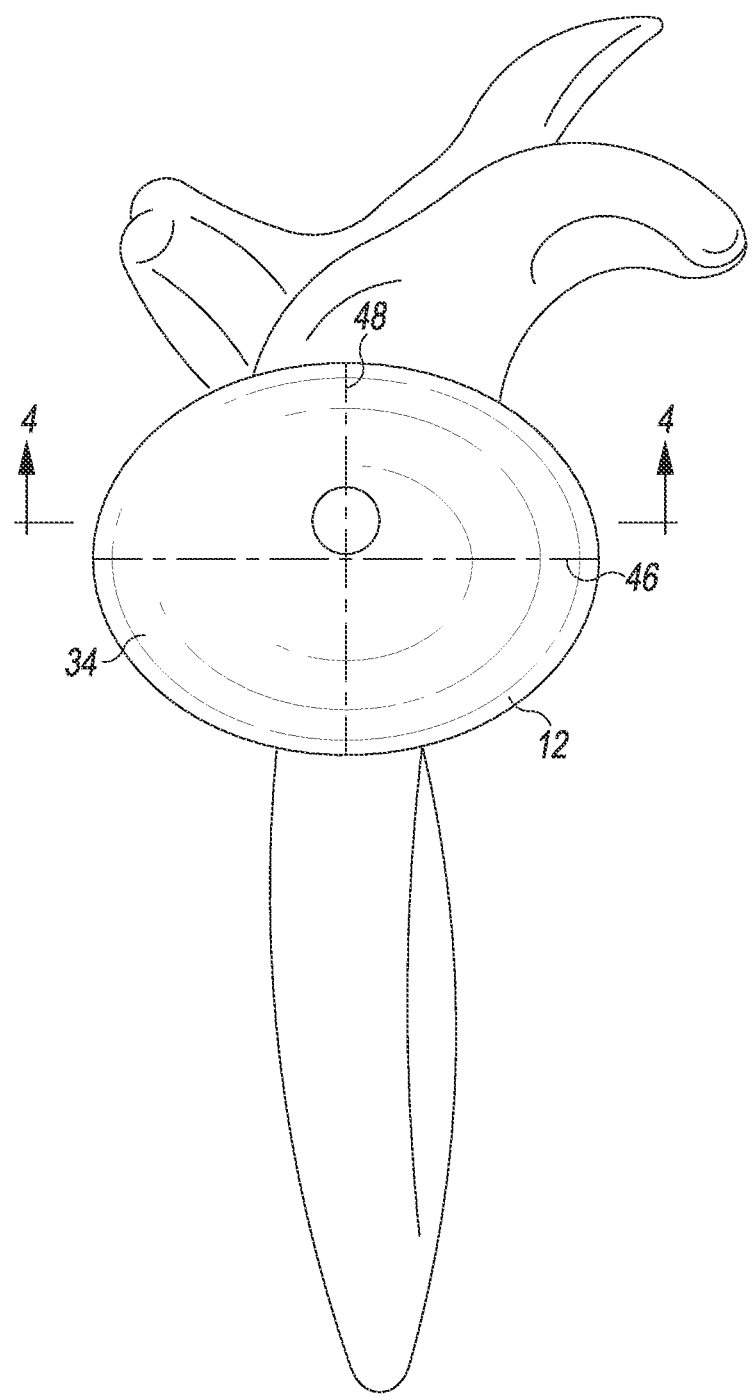
FIG. 2 is a lateral elevational view showing the elliptical glenosphere component of the reverse shoulder orthopaedic implant of FIG. 1 implanted on the scapula of a patient.
Figure 3:
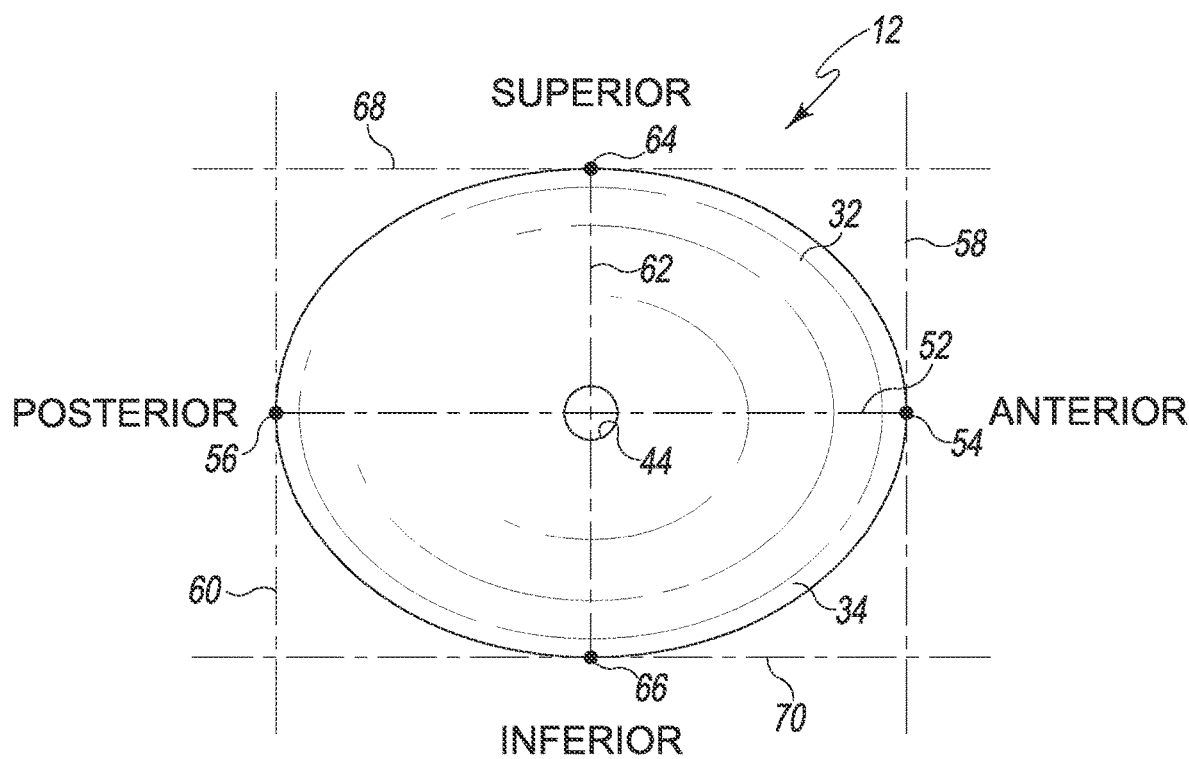
FIG. 3 is an elevational view of the lateral bearing surface of the elliptical glenosphere component of FIG. 2.
Figure 4:
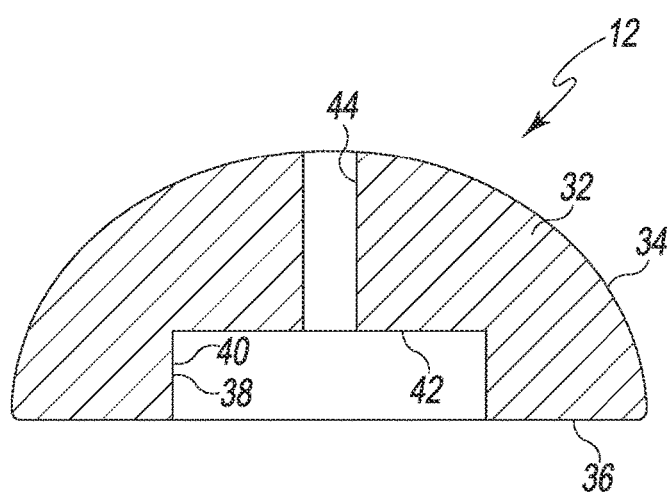
FIG. 4 is a cross sectional view of the elliptical glenosphere component taken along the line 4-4 of FIG. 3, as viewed in the direction of the arrows.

The elliptical glenosphere component 12 includes a body 32 having a curved lateral surface 34. The curved lateral surface 34 of the body 32 provides a smooth bearing surface upon which the bearing surface 24 of the humeral cup 26 articulates. As can be seen in FIG. 2-4, the lateral bearing surface 34 is hemi-ellipsoidal in shape. That is, the lateral bearing surface 34 defines the general shape of ellipsoid sliced in half along its longitudinal plane.

The elliptical glenosphere component 12 also includes a substantially flat medial surface 36 opposite its lateral bearing surface 34. The medial surface 36 has a tapered bore 38 formed therein. The tapered sidewalls 40 defining the bore 38 extend laterally away from the medial surface 36 to a bottom wall 42. As will be discussed below in more detail, an annular-shaped tapered surface of the metaglene component 14 may be inserted into the tapered bore to engage the sidewalls 40 thereby taper locking the elliptical glenosphere component 12 to the metaglene component 14.

As can be seen in FIG. 4, one end of an installation hole 44 opens into the bottom wall 42 of the tapered bore 38, with the other end of the installation hole 44 opening into the lateral bearing surface 34. As will be discussed below in greater detail, a surgical instrument, such as a hex head driver, may be passed through the installation hole 44 during a surgical procedure to implant the elliptical glenosphere component 12.

As alluded to above, unlike conventional hemispherically-shaped components, the glenosphere component 12 described herein is hemi-ellipsoidal in shape. As can be seen in FIGS. 2 and 3, the glenosphere component 12 is wider in the anterior/posterior direction than it is in the superior/inferior direction. Specifically, as can best be seen in FIG. 2, the longitudinal axis 46 of the glenosphere component 12 extends in the anterior/posterior direction, with its shorter lateral axis 48 extending in the superior/inferior direction. This is demonstrated geometrically in the elevational view of the glenosphere component's lateral bearing surface 34 shown in FIG. 3 where both the anterior/posterior and the widths of the glenosphere component 12 are shown as a pair of imaginary line segments extending through the glenosphere component 12 in their respective directions. In particular, an imaginary line segment 52 extends between an anterior-most point 54 of the glenosphere component 12 (i.e., the anterior-most point on the glenosphere component's lateral bearing surface 34) and a posterior-most point 56 (i.e., the posterior-most point on the glenosphere component's lateral bearing surface 34) of the glenosphere component 12. The length of the imaginary line segment 52 defines the anterior/posterior width of the glenosphere component 12. As can be seen in FIG. 3, in the illustrative embodiment described herein, the line segment 52 extends orthogonally between an imaginary tangent line 58 passing through the anterior-most point 54 of the glenosphere component 12 and an imaginary tangent line 60 passing through the posterior-most point 56 of the glenosphere component 12. Similarly, an imaginary line segment 62 extends between a superior-most point 64 of the glenosphere component 12 (i.e., the superior-most point on the glenosphere component's lateral bearing surface 34) and an inferior-most point 66 of the glenosphere component 12 (i.e., the inferior-most point on the glenosphere component's lateral bearing surface 34). As can be seen in FIG. 3, in the illustrative embodiment described herein, the line segment 62 extends orthogonally between an imaginary tangent line 68 passing through the superior-most point 64 of the glenosphere component 12 and an imaginary tangent line 70 passing through the inferior-most point 66 of the glenosphere component 12. The length of the imaginary line segment 62 defines the superior/inferior width of the glenosphere component 12. Because the glenosphere component 12 is wider in the anterior/posterior direction than it is in the superior/inferior direction, the imaginary line segment 52 is longer than the imaginary line segment 62.

It should be appreciated that such an arrangement in which the glenosphere component 12 is wider in the anterior/posterior direction than it is in the superior/inferior direction may reduce the occurrences of notching in some patients. In particular, depending on the anatomy of a specific patient, a glenosphere component that is wider in the anterior/posterior direction than it is in the superior/inferior direction may reduce the occasions in which the medial side of the glenosphere component contacts the scapula relative to a hemispherically-shaped glenosphere component.

Figure 5:
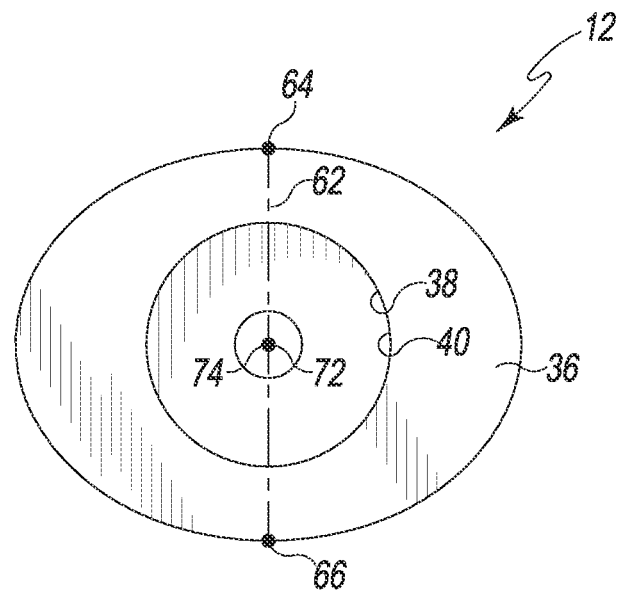
FIG. 5 is a medial elevational view of the elliptical glenosphere component of FIG. 3 showing the tapered bore positioned in a centered position.
Figure 6:
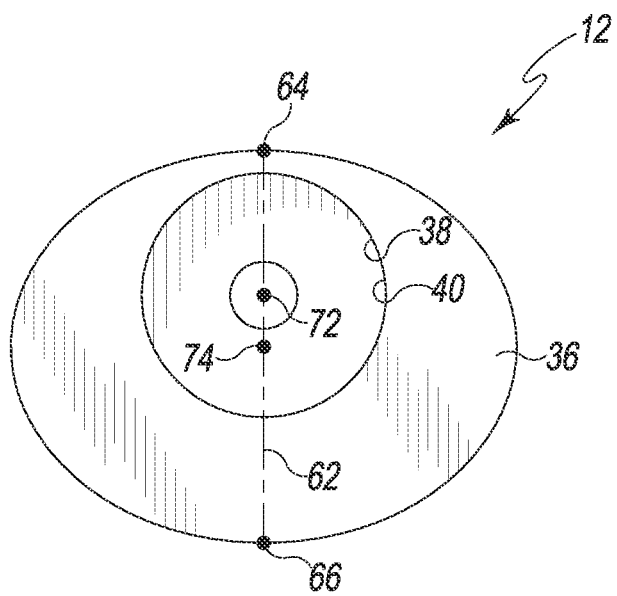
FIG. 6 is a view similar to FIG. 5, but showing the tapered bore positioned in an offset position.
Figure 7:
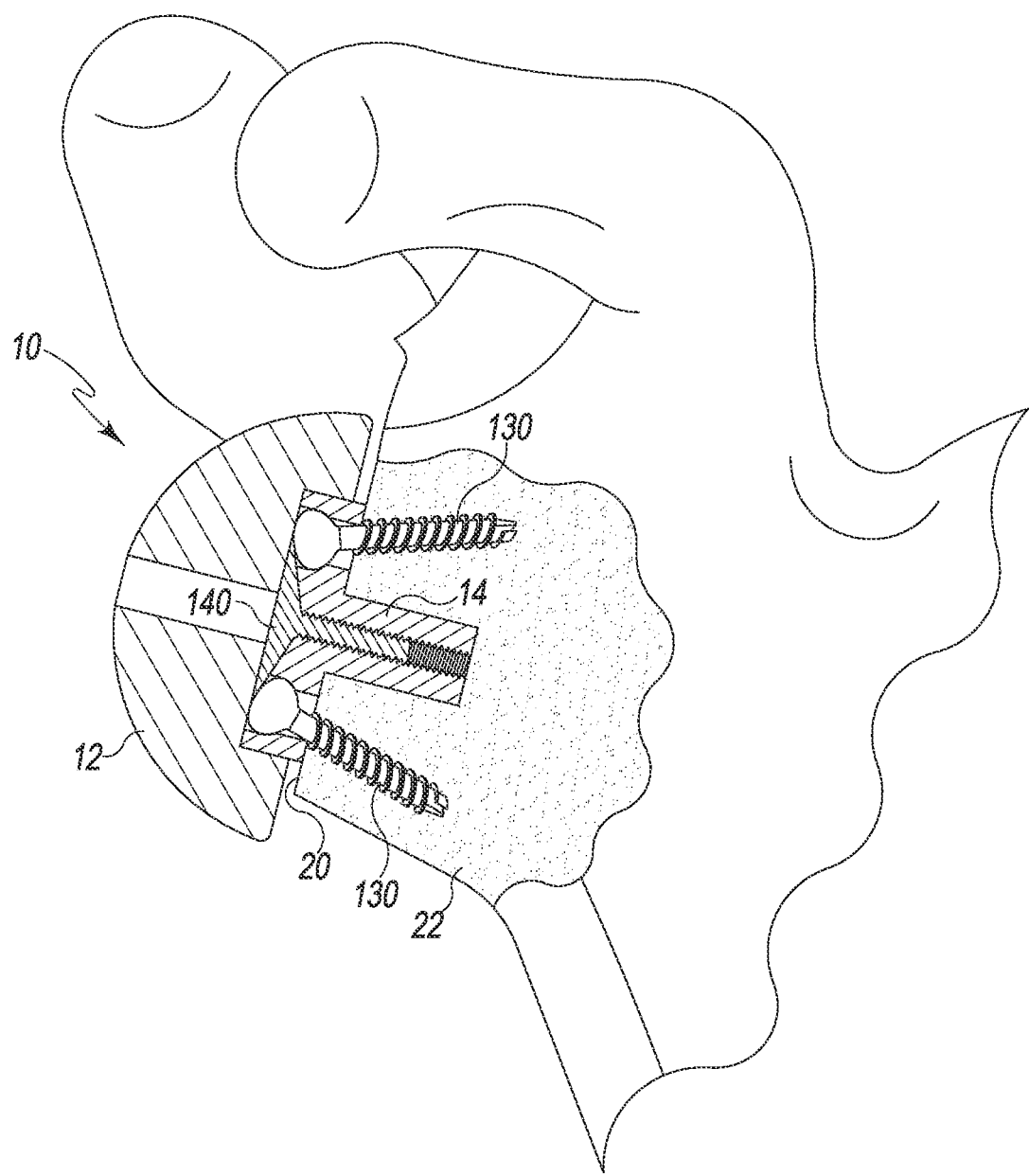
FIG. 7 is a cross sectional view showing the elliptical glenosphere component of FIG. 3 implanted on the scapula of a patient.

As can be seen in the elevational views of the glenosphere component's medial surface 36 shown in FIGS. 5 and 6, the glenosphere component's tapered bore 38 may be centered in the superior/inferior direction (see FIG. 6) or offset superiorly in the superior/inferior direction (see FIG. 7). In particular, the central axis 72 of the tapered bore 38 may be positioned at the center of the superior/inferior width of the elliptical glenosphere component 12, or it may be positioned superiorly of the center of the superior/inferior width of the elliptical glenosphere component 12. The is demonstrated in the elevational views of the glenosphere component's medial surface 36 shown in FIGS. 5 and 6 where the position of the central axis 72 of the tapered bore 38 is shown relative to a midpoint 74 that bisects the imaginary line segment 62 defining the superior/inferior width of the glenosphere component 12. As can be seen in FIG. 5, in the case of a centered glenosphere component 10, the central axis 72 of the tapered bore 38 is positioned on the midpoint 74 of the imaginary line segment 62 defining the superior/inferior width of the glenosphere component 12. However, as can be seen in FIG. 6, in the case of an offset glenosphere component 10, the central axis 72 of the tapered bore 38 is still positioned on the imaginary line segment 62 defining the superior/inferior width of the glenosphere component 12, but is spaced apart from its midpoint 74 in the superior direction. In other words, in the case of an offset glenosphere component 10, the central axis 72 of the tapered bore 38 is positioned on the imaginary line segment 62 at a location between its midpoint 74 and the superior-most point 64.

Such offset of the tapered bore 38 in the superior direction offsets the glenosphere component 12 in the inferior direction when it is secured to the metaglene component 14 implanted in the patient's glenoid surface. Such an implanted offset glenosphere component 12 is shown in FIG. 2. It should be appreciated that such an inferior offset of the glenosphere component 12 may reduce the occurrences of notching in some patients. In particular, depending on the anatomy of a specific patient, a glenosphere component offset inferiorly may reduce the occasions in which the medial side of the glenosphere component contacts the scapula relative to a centered glenosphere component.

It should be appreciated that the tapered bore 38 of the elliptical glenosphere component 12 may also be offset in other directions. For example, the tapered bore 38 of the elliptical glenosphere component 12 may be offset anteriorly or posteriorly relative to the center of the glenosphere component's medial surface 36 (i.e., it may be offset anteriorly or superiorly relative to the midpoint 74 that bisects the imaginary line segment 62). Moreover, the tapered bore 38 of the elliptical glenosphere component 12 may be offset inferiorly relative to the center of the glenosphere component's medial surface 36. Yet, further, the tapered bore 38 of the elliptical glenosphere component 12 may be offset in a combination of directions relative to the center of the glenosphere component's medial surface 36. For example, the tapered bore 38 of the elliptical glenosphere component 12 may be offset both superiorly and anteriorly (or superiorly and posteriorly) relative to the center of the glenosphere component's medial surface 36.

The glenosphere component 12 may be constructed with an implant-grade biocompatible metal, although other materials may also be used. Examples of such metals include cobalt, including cobalt alloys such as a cobalt chrome alloy, titanium, including titanium alloys such as a Ti6Al4V alloy, and stainless steel. The lateral bearing surface 34 of such a metallic glenosphere component 12 may be polished or otherwise treated to enhance its smooth bearing surface.

The glenosphere component 12 may be provided in various different configurations to provide the flexibility necessary to conform to varying anatomies from patient to patient. For example, the glenosphere component 12 may be provided in various superior/inferior diameters to match the needs of a given patient. For example, in one illustrative embodiment, the glenosphere component 12 may be provided in two different superior/inferior diameters—38 mm and 42 mm.

As shown in FIG. 7, the glenosphere component 12 is installed on the metaglene component 14 implanted in the bone tissue of the glenoid surface 20 of the patient's scapula 22. To do so, the surgeon first aligns the glenosphere component 12 relative to the implanted metaglene component 14 such that its tapered bore 38 is aligned with the an annular-shaped tapered outer surface 108 of the metaglene component 14. The surgeon then advances the glenosphere component 12 such that the tapered outer surface 108 of the metaglene component 14 is inserted into the tapered bore 38 of the glenosphere component 12. The surgeon then strikes the glenosphere component 12 (or a head impaction tool positioned thereon) with a surgical mallet, sledge, or other impaction tool to drive the glenosphere component 12 medially so as to urge the sidewalls 40 defining the glenosphere component's tapered bore 38 into contact with the tapered outer surface 108 of the metaglene component 14 thereby taper locking the glenosphere component 12 to the implanted metaglene component 14. Such final assembly of the glenosphere component 12 to the implanted metaglene component 14 is shown in FIGS. 2 and 7.

Figure 8:
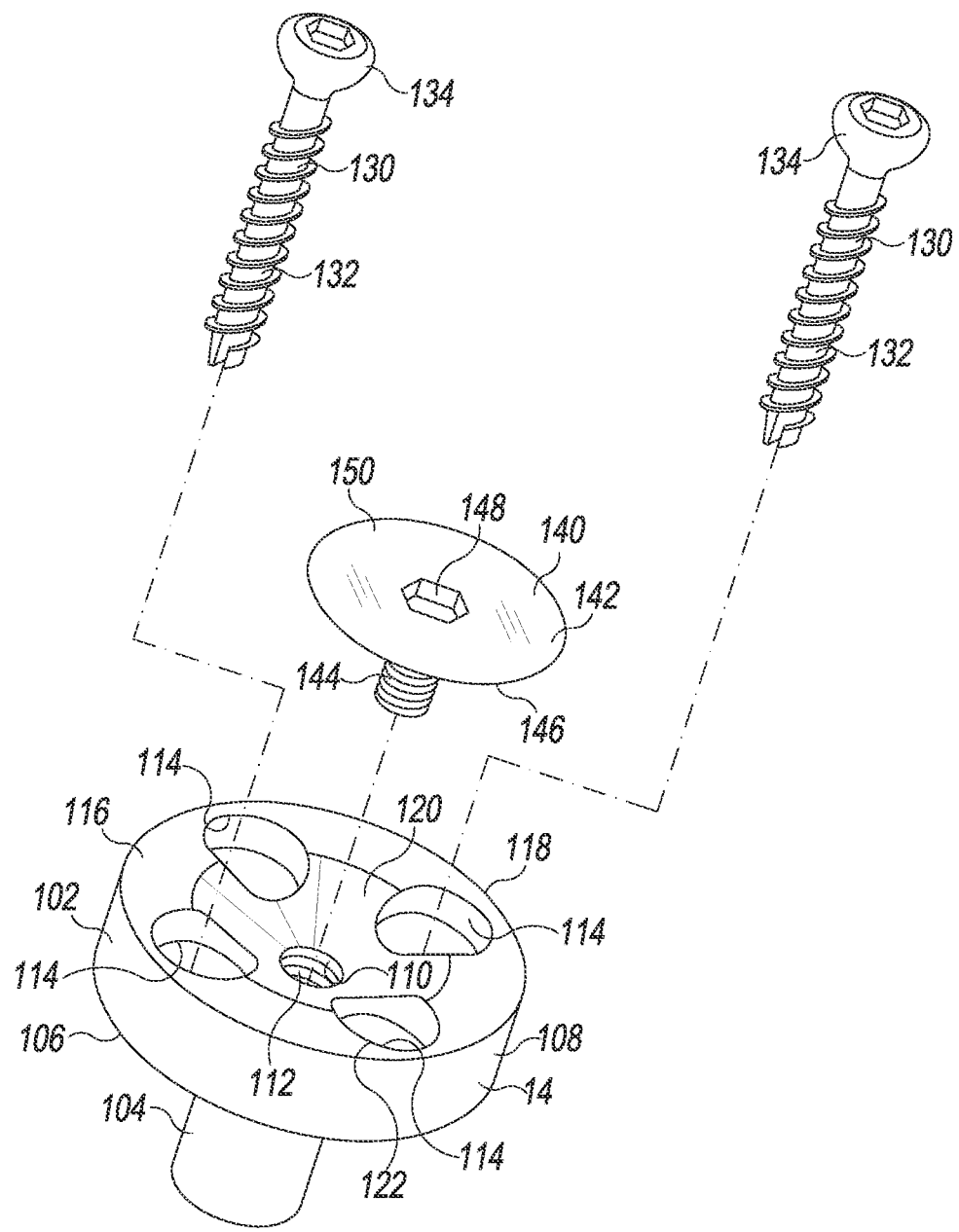
FIG. 8 is an exploded perspective view showing a screw cap used to lock the compression screws within a metaglene component.
Figure 9:
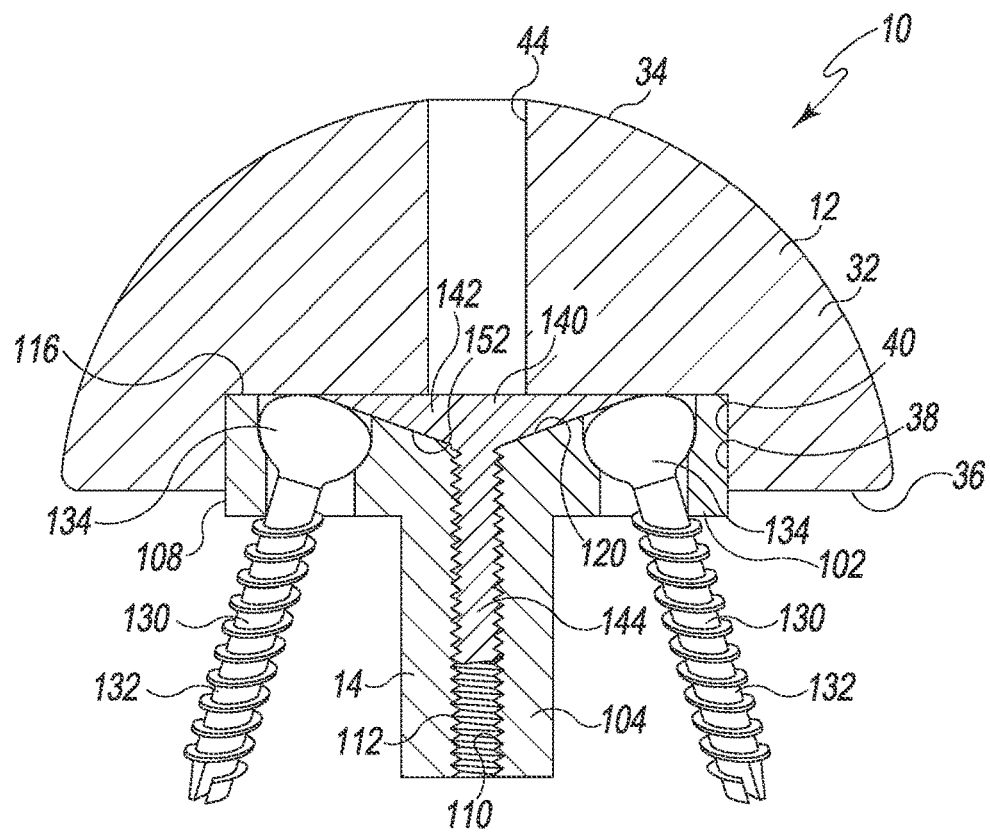
FIG. 9 is a cross sectional view showing the compression screws and screw cap installed on the metaglene component.
Figure 10:
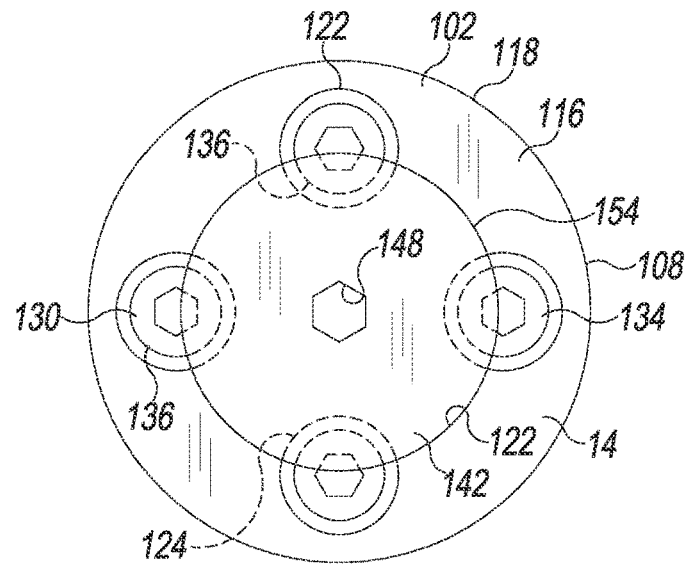
FIG. 10 is a plan view showing the compression screws and screw cap installed on the metaglene component.

Referring now to FIGS. 8-10, there is shown the metaglene component 14 in more detail. The metaglene component 14 includes a platform 102 having a stem 104 extending outwardly from its medial surface 106. The metaglene component's stem 104 is configured to be implanted into the surgically-prepared bone tissue of the glenoid surface 20 of the patient's scapula 22. As described above, the glenosphere component 12 is securable to metaglene component 14. In particular, the outer annular surface 108 of the metaglene component's platform is tapered. As described in detail above, the glenosphere component 12 may be installed on the metaglene component 14 such that the tapered outer surface 108 of the metaglene component 14 is inserted into the tapered bore 38 of the glenosphere component 12. So positioned, the glenosphere component 12 may be driven or otherwise urged toward the metaglene component 14 such that the sidewalls 40 defining the glenosphere component's tapered bore 38 are urged into contact with the tapered outer surface 108 of the metaglene component 14 thereby taper locking the glenosphere component 12 to the metaglene component 14.

As best seen in FIGS. 8 and 9, the metaglene component's stem 104 has a threaded bore 110 formed therein. The threaded bore 110 extends through the entire length of the stem 104, although it could be embodied as a blind bore. A number of threads 112 are formed in the sidewall that defines the threaded bore 110. The threads 112 are sized to match, and hence threadingly receive, the threads of a screw cap 140 and a retraction tool (not shown).

As can be seen in FIGS. 8-10, the metaglene component's platform 102 has a number of screw holes 114 extending therethrough. One end of each of the screw holes 114 opens into the medial surface 106 of the platform 102, with its other end opening into the platform's opposite lateral surface 116. As can be seen best in FIG. 9, each of the screw holes 114 is counterbored to accommodate the screw heads of the compression screws used to secure the metaglene component 12 to the bone tissue of the patient's scapula 22. As such, the upper end of the screw holes 114 has a larger diameter than does the lower end of the screw holes 114. Each of the screw holes 114 is located in one of the four quadrants of the metaglene component's platform 102. As such, each of the screw holes 114 is positioned about 90° from one another.

In the illustrative embodiment described herein, each of the screw holes 114 is spaced radially outwardly from the center of the metaglene component's platform 102 at a position between the threaded bore 110 and the outer annular edge 118 where the platform's lateral surface 116 meets its tapered outer surface 108. As can be seen in FIGS. 8 and 9, the lateral surface 116 of the metaglene component's platform 102 has a countersunk surface 120 formed therein. As can be seen in FIG. 8, each of the screw holes 114 opens partially into the countersunk surface 120 of the metaglene component's platform 102. In particular, as can be seen from the elevational view of the metaglene component's lateral surface 116 shown in FIG. 10, the external boundary or perimeter of each of the screw holes 114 defines a circumference 122. An inner section 124 of the circumference 122 of each of the screw holes 114 (i.e., a section positioned near the center of the metaglene component's platform 102) is positioned within the countersunk surface 120.

The metaglene component 14 may be constructed with an implant-grade biocompatible metal, although other materials may also be used. Examples of such metals include cobalt, including cobalt alloys such as a cobalt chrome alloy, titanium, including titanium alloys such as a Ti6Al4V alloy, and stainless steel. Such a metallic metaglene component 14 may also be coated with a surface treatment, such as hyaluronic acid (HA), to enhance biocompatibility. Moreover, the surfaces of the metaglene component 14 that engage the natural bone, such as the medial surface 106 of platform 102 and the outer surfaces of the stem 104 may be textured to facilitate securing the component to the bone. Such surfaces may also be porous coated to promote bone ingrowth for permanent fixation.

Unlike the glenosphere component 12 that may be provided in various sizes to provide the flexibility necessary to conform to varying anatomies from patient to patient, in the illustrative embodiment described herein, the metaglene component 14 may be provided in a single, "universal" size that accommodates glenosphere components of various sizes. For example, in one illustrative embodiment, a metaglene component 14 may be provided in a single size to accommodate both a 38 mm glenosphere component 12 and a 42 mm glenosphere component 12.

As can be seen in FIGS. 8-10, a compression screw 130 may be positioned in some or all of the screw holes 114 to secure the metaglene component 12 to the bone tissue of the patient's scapula 22. Each of the compression screws 130 includes a threaded shank 132 having a round screw head 134 on an end thereof. The diameter of the threaded shank 132 is smaller than the diameter of the lower end of the counterbored screw holes 114 of the metaglene component 12 so that the threaded shank 132 may pass through the entire length of the screw holes 114. The screw head 134, on the other hand, has a diameter smaller than the upper end of the counterbored screw holes 114, but larger than the lower end of the counterbored screw holes 114. As such, the screw heads 134 of the compression screws 130 are contained in the upper end of the counterbored screw holes 114 when installed in the metaglene component 12.

Like the metaglene component 14, the compression screws 130 may be constructed with an implant-grade biocompatible metal, although other materials may also be used. Examples of such metals include cobalt, including cobalt alloys such as a cobalt chrome alloy, titanium, including titanium alloys such as a Ti6Al4V alloy, and stainless steel.

As can be seen in FIGS. 8-10, a screw cap 140 is secured to the metaglene component 14. The screw cap 140 includes a locking flange 142 having a threaded shaft 144 extending away from its lower surface 146. The screw cap's threaded shaft 144 may be threaded into the threaded bore 110 of the metaglene component's stem 104 to secure the screw cap 140 to the metaglene component. A drive socket 148, such as a hex drive socket, is formed in an upper surface 150 of the screw cap's locking flange 142. A drive tool, such as a hex driver (not shown), may be inserted into the drive socket 148 to drive (i.e., rotate) the screw cap 140 relative to the metaglene component 14. Rotation in one direction (e.g., clockwise) may be used to tighten, and hence secure, the screw cap 140 to the metaglene component 14, with rotation in the opposite direction (e.g., counterclockwise) being used to loosen, and hence, remove the screw cap 140 from the metaglene component 14.

As can be seen in FIG. 9, the lower surface 146 of the screw cap's locking flange 142 defines a generally conical annular-shaped beveled surface 152. The annular-shaped beveled surface 152 is sized and shaped to be received into and closely compliment the countersunk surface 120 of the metaglene component's platform 102. In such a way, the locking flange 142 partially covers the metaglene component's screw holes 114 and hence the heads 134 of the compression screws 130 positioned therein. What is meant herein by "cover" in regard to the position of the locking flange 142 relative to the screw holes 114 of the metaglene component 14 and/or the heads 134 of the compression screws 130 is that the outer annular edge 154 overlays or overlaps at least a section of the circumference 122 of the screw holes 114 and/or the round outer edge 136 of the compression screws 130. This is best demonstrated in the lateral elevational or plan view of FIG. 10. Specifically, when viewed laterally such as the case of FIG. 10, the outer annular edge 154 of the screw cap's locking flange 142 intersects, and hence overlaps, the circumference 122 of each of the screw holes 114 and the round outer edge 136 of each of the compression screws 130. In such a way, the locking flange 142 prevents the compression screws 130 from backing out and escaping the screw holes 114.

As can be seen in FIG. 9, when the screw cap 140 is installed to the metaglene component 14, the annular-shaped beveled surface 152 of the screw cap's locking flange 142 contacts or otherwise engages the round outer edge 136 of each screw head 134 of any of the compression screws 130 installed in the metaglene component 14. Such contact generates a clamping force to resist the compression screws 130 from backing out from the bone tissue of the patient's scapula 22.

Like the metaglene component 14 and the compression screws 130, the screw cap 140 may be constructed with an implant-grade biocompatible metal, although other materials may also be used. Examples of such metals include cobalt, including cobalt alloys such as a cobalt chrome alloy, titanium, including titanium alloys such as a Ti6Al4V alloy, and stainless steel.

As shown in FIG. 7, the metaglene component 14 may first be implanted into the surgically-prepared glenoid surface 20 of the patient's scapula 22 by positioning it at the desired location and orientation, and thereafter fixing it in place by inserting one or more compression screw(s) 130 through the screw holes 114 and driving them into the bone tissue. Once the compression screws 114 have been seated, the surgeon may then install the screw cap 140 by inserting its threaded shaft 144 into the threaded bore 110 of the metaglene component's stem 104 and thereafter rotating the screw cap 140 with a hex driver (not shown) inserted into the drive socket 148 formed in the upper surface 150 of the screw cap's locking flange 142. Tightening of the screw cap 140 in such a manner urges the annular-shaped beveled surface 152 of the screw cap's locking flange 142 into contact with the round outer edge 136 of each screw head 134 of the compression screws 130 installed in the metaglene component 14 thereby asserting a clamping force on the screw heads 134 to resist the compression screws 130 from backing out the bone tissue of the patient's scapula 22. Once the screw cap 140 has been installed, the surgeon may then taper lock the glenosphere component 12 to the implanted metaglene component 14 in the manner described above.

If the metaglene component 14 subsequently needs to be removed during, for example, a revision procedure, the surgeon may first remove the glenosphere component 12 from the implanted metaglene component 14 by breaking the taper lock connection between the two components and lifting the glenosphere component 12 away. Thereafter, the surgeon may insert a hex driver (not shown) into the drive socket 148 formed in the upper surface 150 of the screw cap's locking flange 142 and rotating the screw cap 140 in a direction opposite to the direction used to install the screw cap 140. Loosening of the screw cap in such a manner moves the annular-shaped beveled surface 152 of the screw cap's locking flange 142 out of contact with the round outer edge 136 of each screw head 134 of the compression screws 130 installed in the metaglene component 14 thereby releasing the clamping force from the screw heads 134. Continued loosening of the screw cap 140 allows its threaded shaft 144 to escape the threaded bore 110 of the metaglene component's stem 104 thereby allowing the screw cap 140 to be lifted away. Thereafter, the surgeon may use a drive tool (not shown) to remove the compression screws 130. An extraction tool (not shown) may be threaded into the threaded bore 110 of the metaglene component's stem 104 and thereafter used to extract the metaglene component 14 from the bone tissue of the patient's scapula 22.

Figure 11:
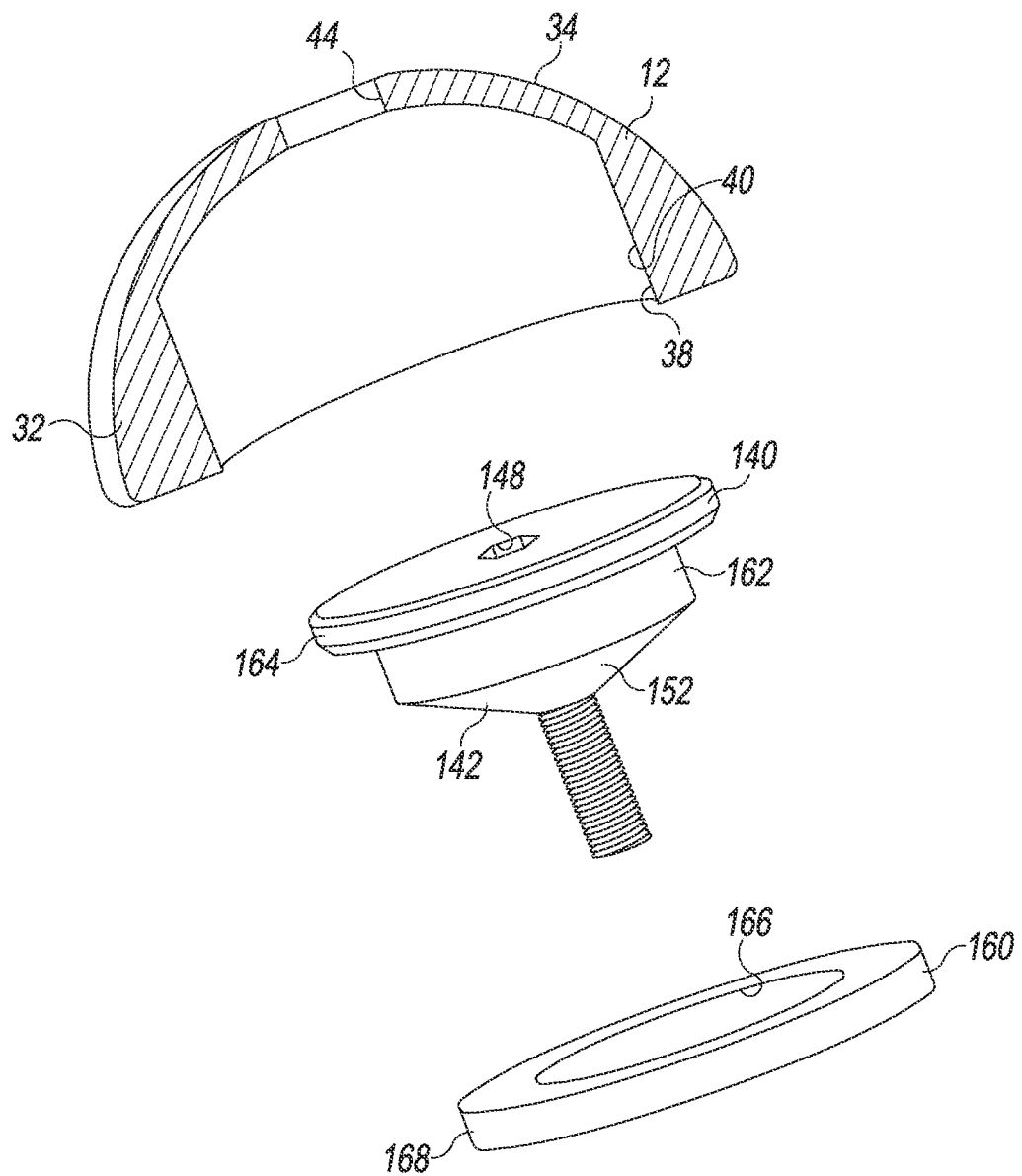
FIG. 11 is an exploded perspective view showing a screw cap that is captured in a glenosphere component and used to lock the compression screws within a metaglene component.
Figure 12:
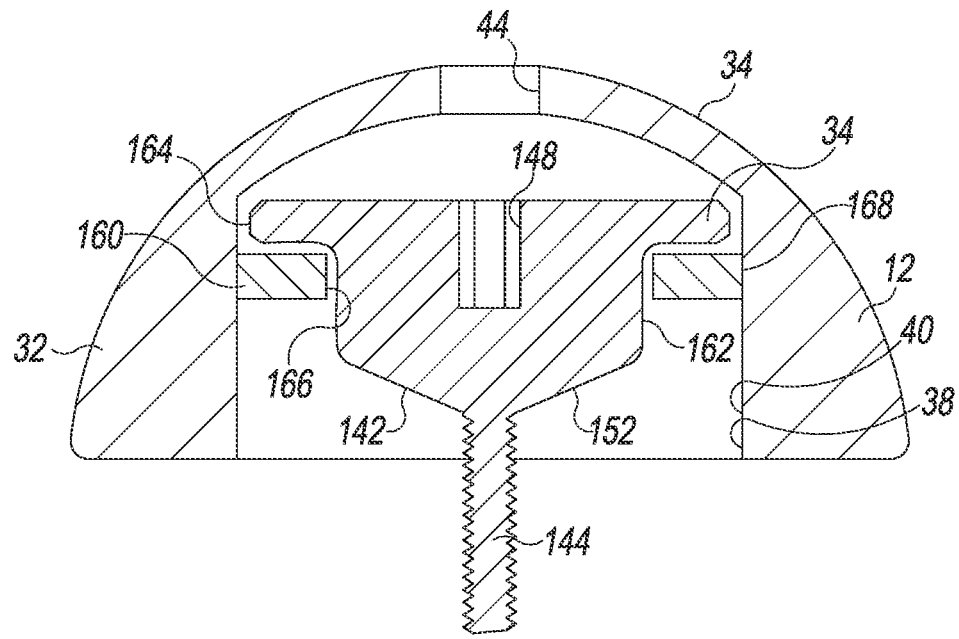
FIG. 12 is an assembled cross sectional view showing the screw cap captured in the glenosphere component by the retaining ring.
Figure 13:
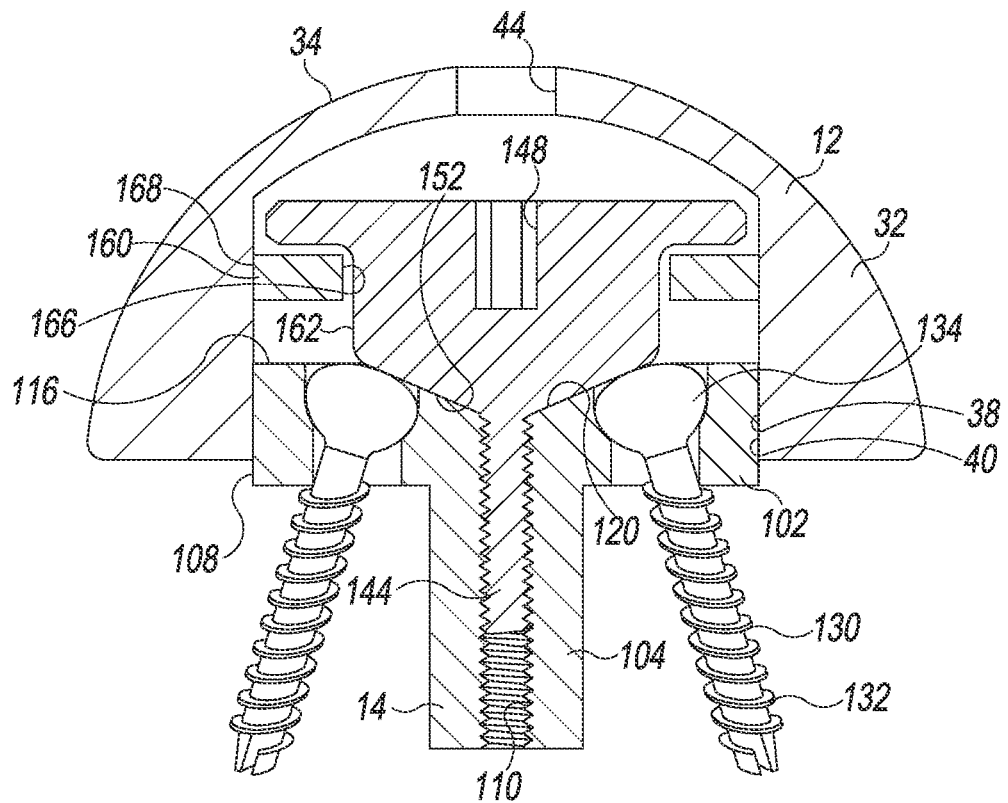
FIG. 13 is a view similar to FIG. 12, but showing the glenosphere component secured to the metaglene component.

Referring now to FIGS. 11-13, there is shown an embodiment in which the screw cap 140 is captured in the glenosphere component 14. In such an embodiment, slight modification has been made to the glenosphere component 14 and the screw cap 140 as shown in FIGS. 11-13. The same reference numerals are used in FIGS. 11-13 to designate components similar to those discussed above in regard to FIGS. 1-10. As can be seen in FIG. 11, the screw cap 140 is captured and retained in the tapered bore 38 of the glenosphere component 12 by a retaining ring 160. To do so, the screw cap 140 of the design of FIGS. 11-13 includes a cylindrically-shaped surface 162 that mates at one end with the annular-shaped beveled surface 152 of the screw cap's locking flange 142 and at its opposite end with an annular retaining flange 164. The retaining ring 160 is captured on the cylindrically-shaped surface 162 of the screw cap 140. That is, the cylindrically-shaped surface 162 of the screw cap 140 is positioned in the retaining ring's opening 166. As can be seen in FIGS. 11 and 12, the inner diameter of the retaining ring 160 (i.e., the diameter of its opening 166) is greater than the diameter of the cylindrically-shaped surface 162 of the screw cap 140, but less than the diameter of the screw cap's retaining flange 164. The outer diameter of the retaining ring 160 (i.e., the diameter of its outer surface 168) is greater than the diameter of the screw cap's retaining flange 16 and is sized and configured to be press fit, welded (or press fit and welded), or taper locked to the tapered sidewalls 40 defining the glenosphere component's tapered bore 38. As such, when assembled, the retaining ring 160 captures the screw cap 140 in the glenosphere component's tapered bore 38. So captured, both free rotation and limited linear movement of the screw cap 140 relative to the glenosphere component 12 are allowed, but it is prevented from escaping the glenosphere component's tapered bore 38.

The design of FIGS. 11-13 may be installed in a similar manner to as described above in regard to the design of FIGS. 8-10. In particular, the metaglene component 14 may first be implanted into the surgically-prepared glenoid surface 20 of the patient's scapula 22 by positioning it at the desired location and orientation, and thereafter fixing it in place by inserting one or more compression screw(s) 130 through the screw holes 114 and driving them into the bone tissue. Once the compression screws 114 have been seated, the surgeon may then install the glenosphere component 12, and hence the screw cap 140 captured therein, by inserting the screw cap's threaded shaft 144 into the threaded bore 110 of the metaglene component's stem 104. Thereafter, the drive tip of a hex driver (not shown) may be advanced through the glenosphere component's installation hole 44 and into the screw cap's drive socket 148. The surgeon then rotates the screw cap 140 with the hex driver. Such tightening of the screw cap 140 urges the annular-shaped beveled surface 152 of the screw cap's locking flange 142 into contact with the round outer edge 136 of each screw head 134 of the compression screws 130 installed in the metaglene component 14 thereby asserting a clamping force on the screw heads 134 to resist the compression screws 130 from backing out of the bone tissue of the patient's scapula 22. Once the screw cap 140 has been installed, the surgeon may then taper lock the glenosphere component 12 to the implanted metaglene component 14 in the manner described above.

If the metaglene component 14 subsequently needs to be removed during, for example, a revision procedure, the surgeon may first remove the glenosphere component 12, and hence the captured screw cap 140, from the implanted metaglene component 14 by inserting the drive tip of a hex driver through the glenosphere component's installation hole 44 and into the screw cap's drive socket 148. The surgeon then rotates the screw cap 140 with the hex driver in a direction opposite to the direction used to install the screw cap 140. Loosening of the screw cap in such a manner moves the annular-shaped beveled surface 152 of the screw cap's locking flange 142 out of contact with the round outer edge 136 of each screw head 134 of the compression screws 130 installed in the metaglene component 14 thereby releasing the clamping force from the screw heads 134. The surgeon may then break the taper lock connection between the glenosphere component 12 and the metaglene component 14 and continue loosening the screw cap 140 until its threaded shaft 144 escapes the threaded bore 110 of the metaglene component's stem 104 thereby allowing the glenosphere component 12, and hence the screw cap 140 captured therein, to be lifted away from the metaglene component 14. Thereafter, the surgeon may use a drive tool (not shown) to remove the compression screws 130. An extraction tool (not shown) may be threaded into the threaded bore 110 of the metaglene component's stem 104 and thereafter used to extract the metaglene component 14 from the bone tissue of the patient's scapula 22.

It should be appreciated that the screw caps 140 described above in regard to FIGS. 8-13 provide efficiency during a surgical procedure to implant the metaglene component 14. For example, the screw caps 140 allow for implantation of the metaglene component 14 without the use of self-locking surgical screws. Surgical installation of self-locking surgical screws requires the use of a guide wire and other surgical considerations. By providing a locking function, the screw cap 140 allows compression screws, which are much easier to surgically install, to be used in lieu of self-locking surgical screws.

It should be appreciated that the concepts and features disclosed herein may be used in various combinations with one another or independently of one another. For example, the elliptical glenosphere component 12 of FIGS. 1-6 may be used in combination with either the metaglene component 14 of FIGS. 8-10 or the metaglene component 14 of FIGS. 11-13. Moreover, the elliptical glenosphere component 12 of FIGS. 1-6 may be used in combination with other metaglene components, including metaglene components without the screw caps 140 described herein. Similarly, the metaglene component 14 of FIGS. 8-10 may be used in combination with the elliptical glenosphere component 12 of FIGS. 1-6, or, alternatively, may be used with a conventional hemispherically-shaped or other type of glenosphere component. Along the same line, the metaglene component 14 of FIGS. 11-13 may be used in combination with the elliptical glenosphere component 12 of FIGS. 1-6, or, alternatively, may be used with a conventional hemispherically-shaped or other type of glenosphere component.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure as defined by the appended claims.

The invention claimed is:

1. A method of surgically implanting a reverse shoulder orthopaedic implant, the method comprising:
    implanting a metaglene component in bone tissue of a glenoid surface of a scapula with a plurality of bone screws, the metaglene component having an elongated stem with a threaded bore formed therein; and
    installing a glenosphere component having a bore formed therein over the metaglene component such that the metaglene component is at least partially received within the bore of the glenosphere component, wherein coupling the glenosphere component comprises inserting a tool through an installation hole formed in the glenosphere component to engage the tool with a drive socket defined in a retraining flange of a screw cap captured in the bore of the glenosphere component via a retaining ring and using the tool to thread a threaded shaft of the screw cap into the threaded bore of the metaglene component to secure the glenosphere component to the metaglene component such that a locking flange of the screw cap is positioned at least partially over a head of each of the plurality of bone screws.

2. The method of claim 1, wherein inserting the tool comprises inserting the tool through an installation hole opening at a first end into a lateral bearing surface of the glenosphere component and at a second end into the bore of the glenosphere component.

3. The method of claim 1, wherein using the tool to thread a threaded shaft of the screw cap into the threaded bore of the metaglene component comprises rotating the tool to thread the threaded shaft of the screw cap within the threaded bore of the elongated stem of the metaglene component.

4. The method of claim 3, further comprising rotating the tool to at least partially disengage the threaded shaft of the screw cap from a threaded connection with the threaded bore of the elongated stem of the metaglene component.

5. The method of claim 1, further comprising breaking a taper lock connection between the glenosphere component and the implanted metaglene component to remove the glenosphere component from the implanted metaglene component.

6. The method of claim 5, further comprising:
    reinserting, subsequent to installing the glenosphere component, the tool through the installation hole formed in the glenosphere component to engage the tool with the drive socket defined in the retaining flange of the screw cap; and
    rotating the tool to disengage the threaded shaft of the screw cap from a threaded connection with the threaded bore of the elongated stem of the metaglene component, subsequent to the step of breaking a taper lock connection between the glenosphere component and the implanted metaglene component.

7. The method of claim 6, further comprising:
    threading a second tool into the threaded bore formed in the elongated stem of the metaglene component in place of the threaded shaft of the screw cap, and operating the second tool to extract the metaglene component from the glenoid surface of the scapula.

8. The method of claim 1, wherein implanting the metaglene component in the bone tissue of the glenoid surface of the scapula is preformed prior to installing the glenosphere component over the metaglene component.

9. The method of claim 1, wherein implanting the metaglene component includes positioning each of the plurality of bone screws into a corresponding screw hole extending through the metaglene component.

10. The method of claim 1, wherein using the tool comprises threading the threaded shaft of the screw cap within the threaded bore of the metaglene component by engaging threads on an outer surface of the threaded shaft of the screw cap with threads on an inner surface of the threaded bore formed in the elongated stem of the metaglene component.

11. The method of claim 1, wherein using the tool to thread the threaded shaft of the screw cap into the threaded bore of the metaglene component comprises rotating the screw cap within the bore of the glenosphere component while the screw cap is retained in the bore of the glenosphere component by the retaining ring.

12. The method of claim 11, wherein rotating the screw cap within the bore of the glenosphere component comprises rotating the retaining flange of the screw cap on the retaining ring.

13. The method of claim 11, wherein rotating the screw cap within the bore of the glenosphere component comprises rotating a cylindrical body of the screw cap within an opening of the retaining ring.

14. The method of claim 1, wherein using the tool to thread the threaded shaft of the screw cap into the threaded bore of the metaglene component comprises using the tool to thread the threaded shaft of the screw cap into the threaded bore of the metaglene component such that an annular-shaped beveled surface of the locking flange is in contact with a screw head of each of the plurality of bone screws.

15. The method of claim 1, wherein using the tool to thread the threaded shaft of the screw cap into the threaded bore of the metaglene component comprises using the tool to thread the threaded shaft of the screw cap into the threaded bore of the metaglene component such that an annular-shaped beveled surface of the locking flange engages a countersunk surface of a platform of the metaglene component.

16. The method of claim 15, wherein using the tool to thread the threaded shaft of the screw cap into the threaded bore of the metaglene component comprises using the tool to thread the threaded shaft of the screw cap into the threaded bore of the metaglene component such that the retaining flange of the screw cap contacts the retaining ring when the locking flange engages the countersunk surface of the platform.

17. The method of claim 1, further comprising:
inserting the retaining ring into the bore of the glenosphere; and
taper locking the retaining ring into the bore of the glenosphere.

18. The method of claim 1, wherein installing the glenosphere component over the metaglene component comprises taper locking the glenosphere component to the metaglene component by engaging an outermost periphery of a platform of the metaglene component with sidewalls defining the bore of the glenosphere component such that at least a portion of the platform and the screw cap are disposed within the bore.

19. The method of claim 1, wherein installing the glenosphere component over the metaglene component comprises aligning the installation hole formed in the glenosphere component with the drive socketed defined in the retaining flange of the screw cap.

20. The method of claim 1, wherein (i) an anterior/posterior width is defined by a distance between an anterior-most point of the glenosphere component and a posterior-most point of the glenosphere component, (ii) a superior/inferior width is defined by a distance between a superior-most point of the glenosphere component and an inferior-most point of the glenosphere component, (iii) the anterior-posterior width of the glenosphere component is greater than the superior-inferior width of the glenosphere component, (iv) an imaginary line segment extends from the superior-most point of the glenosphere component to the inferior-most point of the glenosphere component, and (v) the center of the bore formed in the glenosphere component is positioned between the midpoint of the imaginary line segment and the superior-most point of the glenosphere component.

* * * * *